United States Patent [19]

Kompis et al.

[11] Patent Number: 4,515,948
[45] Date of Patent: May 7, 1985

[54] 2,4-DIAMINO-5-(4-AMINO AND 4-DIMETHYLAMINO-3,5-DIMETHOXY BENZYL)PYRIMIDINES

[75] Inventors: Ivan Kompis, Oberwil; Gérald Rey-Bellet, Basel; Guido Zanetti, Füllinsdorf, all of Switzerland

[73] Assignee: Hoffmann-La Roche Inc., Nutley, N.J.

[21] Appl. No.: 279,106

[22] Filed: Jun. 30, 1981

Related U.S. Application Data

[60] Division of Ser. No. 63,292, Aug. 2, 1979, abandoned, which is a continuation-in-part of Ser. No. 795,828, May 11, 1977, abandoned, which is a continuation-in-part of Ser. No. 504,416, Sep. 9, 1974, abandoned.

[30] Foreign Application Priority Data

Sep. 12, 1973 [CH] Switzerland ............... 13057/73
Jul. 22, 1974 [CH] Switzerland ............... 10063/74

[51] Int. Cl.³ ............................................. C07D 239/48
[52] U.S. Cl. .................................................. 544/325
[58] Field of Search ........................................ 544/325

[56] References Cited

U.S. PATENT DOCUMENTS 2,670,351  2/1954  Jacob ................................. 544/325
3,692,787  9/1982  Roth et al. ....................... 544/325

OTHER PUBLICATIONS

Roth J. Med. Pharm. Chem. 5, (1962), pp. 1103-1125.
Falco et al., JACS vol. 23, pp. 3258-3262, (1951).

Primary Examiner—Glennon H. Hollrah
Assistant Examiner—D. B. Springer
Attorney, Agent, or Firm—Jon S. Saxe; Bernard S. Leon; Matthew Boxer

[57] ABSTRACT

2,4-Diamino-5-benzylpyrimidines of the formula

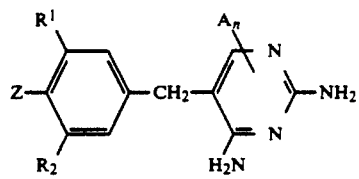

wherein $R^1$, $R^2$, A, Z and n are as hereinafter set forth, are described. The 2,4-diamino-5-benzylpyrimidines of the invention have useful antibacterial activity. More particularly, they inhibit bacterial dihydrofolate reductase and potentiate the antibacterial activity of sulfonamides.

4 Claims, No Drawings

2,4-DIAMINO-5-(4-AMINO AND 4-DIMETHYLAMINO-3,5-DIMETHOXY BENZYL)PYRIMIDINES

This is a division, of application Ser. No. 63,292 filed Aug. 2, 1979, now abandoned which in turn is a continuation of U.S. patent application Ser. No. 795,828, filed May 11, 1977, now abandoned, which in turn is a continuation of Ser. No. 504,416, filed Sept. 9, 1974, now abandoned.

BRIEF SUMMARY OF THE INVENTION

The invention relates to benzylpyrimidines of the formula

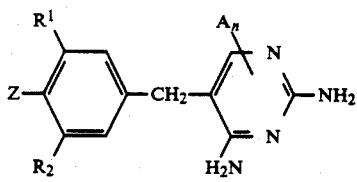

wherein $R^1$ and $R^2$, independently, are $C_{1-3}$ alkyl, $C_{1-3}$ alkoxy, $C_{2-3}$ alkenyl or $C_{2-3}$ alkenyloxy; Z is nitro, amino, pyrrolo, pyrrolidino, piperidino, $-NHR^4$, $-N(R^4)_2$, $-NHR^5$, $-N(R^4)(R^5)$, $-NR^4COOR^4$, $-NHCOOR^4$, $-NHCONHR^3$, $-NHCSNHR^3$, $-N_3$, $-N=N-N(R^4)_2$, $-N(NO)R^4$ or $-NR^3-NH_2$, wherein $R^4$ is $C_{1-3}$ alkyl or $C_{2-3}$ alkenyl, $R^5$ is acyl and $R^3$ is hydrogen, $C_{1-3}$ alkyl or $C_{2-3}$ alkenyl; A is an oxygen atom bonded to one of the cyclic nitrogen atoms; and n is zero or 1.

The compounds of formula I are useful as antibacterial agents and as potentiators of the antibacterial activity of sulfonamides.

DETAILED DESCRIPTION OF THE INVENTION

As used herein, the terms "$C_{1-3}$" and "$C_{2-3}$" denote that the groups prefixed by either of said terms contain 1 to 3 or 2 to 3 carbon atoms, respectively. The term "lower alkyl" denotes straight-chain or branched chain saturated aliphatic hydrocarbons of 1 to 7 carbon atoms, such as methyl, ethyl, propyl, isopropyl, butyl, heptyl and the like. The term "lower alkoxy" denotes a straight chain or branched chain saturated aliphatic ether wherein the alkyl moiety is as hereinbefore described, for example, methoxy, ethoxy, propoxy, isopropoxy, heptyloxy and the like. The term "lower alkylene" denotes a hydrocarbon radical of 2 to 5 carbon atoms, preferably of 2 to 3 carbon atoms, such as ethylene, propylene, butylene and pentylene. The term "lower alkenyl" denotes a straight-chain or branched chain olefinically unsaturated hydrocarbon of 2 to 3 carbon atoms, such as vinyl and allyl. The term "lower alkenyloxy" denotes a straight chain or branched chain olefinically unsaturated hydrocarbon wherein the alkenyl moiety is as hereinbefore described, for example, vinyloxy and allyloxy. The term "acyl" denotes a group which is derived from aliphatic, araliphatic, aromatic, hetero-aromatic carboxylic acids or thiocarboxylic acids, or from aliphatic or aromatic sulfonic acids. Preferred acyl groups are derived from $C_{1-4}$ aliphatic monocarboxylic acids, exemplified by $C_{1-4}$ alkanoyl, such as formyl, acetyl, propionyl and butyryl, and $C_{1-4}$ alkanoyl bearing a lower alkyloxy substituent such as ethoxyacetyl; monocyclic aromatic and aromatic sulfonic acids, exemplified by benzoyl, toluoyl and tosyl; and aliphatic sulfonic acids, exemplified by mesyl. Examples of heteroaromatic acids are, for example, pyridinecarboxylic acids such as nicotinic acid; and thiophenecarboxylic acids. Examples of thiocarboxylic acids are thioacetic acid, thiopropionic acid and the like.

The benzylpyrimidine derivatives of the invention are characterized by the formula

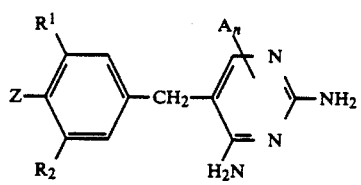

wherein $R^1$ and $R^2$, independently, are $C_{1-3}$ alkyl, $C_{1-3}$ alkoxy, $C_{2-3}$ alkenyl or $C_{2-3}$ alkenyloxy; Z is nitro, amino, pyrrolo, pyrrolidino, piperidino, $-NHR^4$, $-N(R^4)_2$, $-NHR^5$, $-N(R^4)(R^5)$, $-NR^4COOR^4$, $-NHCOOR^4$, $-NHCONHR^3$, $-NHCSNHR^3$, $-N_3$, $-N=N-N(R^4)_2$, $-N(NO)R^4$ or $-NR^3-NH_2$, wherein $R^4$ is $C_{1-3}$ alkyl or $C_{2-3}$ alkenyl, $R^5$ is acyl and $R^3$ is hydrogen, $C_{1-3}$ alkyl or $C_{2-3}$ alkenyl; A is an oxygen atom bonded to one of the cyclic nitrogen atoms; and n is zero or 1, or pharmaceutically acceptable acid addition salts thereof.

A preferred subgenus of the compounds of formula I comprises those wherein Z is nitro, amino, pyrrolo, pyrrolidino, piperidino, $-NHR^4$, $-N(R^4)_2$, $-NHR^5$, $-N(R^4)(R^5)$, $-NR^4COOR^4$, $-NHCOOR^4$, $-NHCONHR^3$ or $-NHCSNHR^3$.

Especially preferred compounds of formula I are those wherein Z is nitro, amino, $-NHR^4$, $-N(R^4)_2$, $-NHR^5$, $-NR^4COOR^4$, $-NHCOOR^4$, $-N_3$,

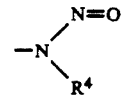

or pyrrolo.

Of the preferred compounds of formula I mentioned above, those wherein $R^1$ and $R^2$ are $C_{1-3}$ alkoxy, particularly methoxy or ethoxy, are most preferred. Also preferred, are those compounds of formula I wherein Z is amino and n is zero.

The benzylpyrimidine derivatives of formula I and their salts are prepared by:

(a) reacting a compound of the formula

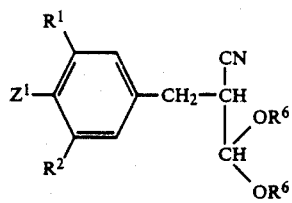

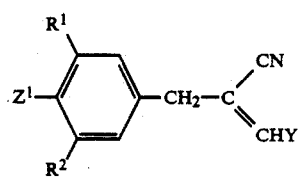

wherein $Z^1$ is nitro, amino, pyrrolo, pyrrolidino, piperidino, —NHR$^4$, —N(R$^4$)$_2$, —NHR$^5$, —N(R$^4$)(R$^5$), —NR$^4$COOR$^4$, —NHCOOR$^4$, —NHCONHR$^3$, —NHCSNHR$^3$ or —NR$^3$NH$_2$, R$^6$ is lower alkyl or taken together with the other R$^6$ is lower alkylene, Y is a leaving group and R$^1$, R$^2$, R$^3$, R$^4$ and R$^5$ are as previously described, with guanidine; or (b) reacting a compound of the formula

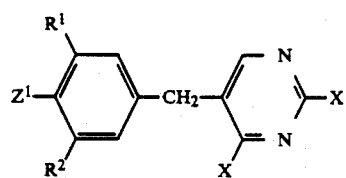

wherein X is chlorine, bromine, lower alkylmercapto, lower alkylsulfonyl or amino, provided that at least one X is other than amino, and $Z^1$, $R^1$ and $R^2$ are as previously described, with ammonia; or (c) reductively removing the substituent $X^1$ in a compound of the formula

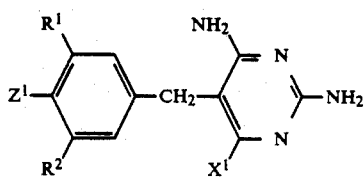

wherein $X^1$ is chlorine, bromine or hydroxy, and $R^1$, $R^2$ and $Z^1$ are as previously described;

or (d) diazotizing a compound of formula I wherein Z is amino and subsequently reacting the diazotized product with sodium azide, with an amine of the formula NH(R$^4$)$_2$ or with an alkali sulfite; or (e) treating a compound of formula I wherein Z is —NHR$^4$ with nitric acid; or (f) converting $Z^2$ in a compound of the formula

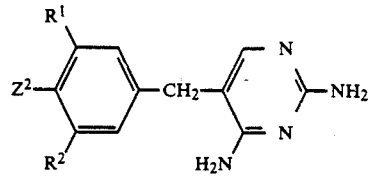

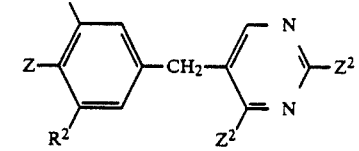

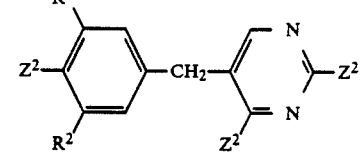

wherein $R^1$, $R^2$ and Z are as previously described and $Z^2$, which can be the same or different in formula Vb or Vc, is a group which can be converted by reduction or hydrolysis into amino or —NHR$^4$, (g) alkylating or alkenylating the group denoted by $Z^3$ in a compound of the formula

wherein $Z^3$ is —NHR$^5$ or —NHCOOR$^4$ and $R^1$, $R^2$, $R^4$ and $R^5$ are as previously described;

or (h) reducing a compound of formula I wherein Z is —N(NO)R$^4$ with Zn/CH$_3$COOH; or (i) subjecting a compound of formula I wherein n is zero to N-oxidation and converting a compound of formula I so obtained into a salt, if desired.

According to process embodiment (a), a compound of formula IIa or IIb is reacted with guanidine. The symbol Y in a compound of formula IIb is a leaving group. Examples of suitable leaving groups are ether groups, for example, lower alkoxy groups, such as methoxy and ethoxy; thioether groups, for example, lower alkylthio groups, such as methylthio and ethylthio; or amino groups derived from primary or secondary amines. Examples of such amino groups are (1) groups derived from primary aliphatic, aryl-aliphatic or aromatic amines, for example, lower alkylamino; benzylamino; and arylamino, such as naphthylamino and especially phenylamino(anilino) which may be substituted in the phenyl ring by one or more halogen, lower alkyl or lower alkoxy groups, or (2) groups derived from secondary aliphatic, aromatic or heterocyclic amines, for example, N,N-di(lower alkyl)amino; N-

(lower alkyl)-N-arylamino, such as N-methyl-N-phenylamino (N-methylanilino) which may be substituted in the phenyl ring by one or more halogen, lower alkyl or lower alkoxy groups; pyrrolidino; piperidino; piperazino; morpholino and the like. An especially preferred amino leaving group is anilino.

The reaction of a compound of formula IIa or IIb with guanidine can be carried out according to known methods as described in Belgian Patent Specification Nos. 594,131; 671,982 and 746,846. In particular, the reaction can be carried out in a solvent, for example, an alkanol such as methanol or ethanol, dimethylformamide dimethylsulfoxide or N-methylpyrazolone at a temperature in the range of from about 25° C. to about 200° C., preferably at a temperature in the range of from about 50° C. to about 170° C.

The compounds of formula IIb can be formed in situ under the conditions of the reaction from the tautomeric compounds of the formula

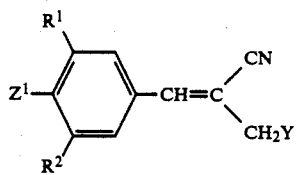

IIc wherein $R^1$, $R^2$, $Z^1$ and Y are as previously described. The compounds of formulas IIb and IIc can occur as the cis or trans isomers or as mixtures thereof.

Process embodiment (a) provides compounds of formula I wherein n is zero, Z has any of the values accorded to $Z^1$ hereinbefore and $R^1$, $R^2$ and $Z^1$ are as previously described.

In accordance with process embodiment (b), a compound of formula III is reacted with ammonia, whereby the bromine, chlorine, lower alkylmercapto or lower alkylsulfonyl group present in the pyrimidine nucleus is replaced by amino. This reaction is conveniently carried out in an alkanolic solution, preferably in a methanolic solution. In a preferred aspect, the reaction is carried out using methanolic ammonia. The reaction is conveniently carried out at a temperature in the range of between about 80° C. and about 200° C., preferably at a temperature in the range of between about 100° C. and about 150° C. Since these temperatures lie above the boiling point of methanol, the reaction is carried out in a closed system, for example, in an autoclave.

Process embodiment (b) provides compounds of formula I wherein n is zero, Z has any of the values accorded to $Z^1$ hereinbefore and $R^1$ and $R^2$ are as previously described.

The removal of a bromine or chlorine group from a compound of formula IV, in accordance with process embodiment (c), can be carried out by treatment with a reducing agent, for example, hydrogen iodide, or catalytically activated hydrogen, for example, palladium in alcohol or with zinc and glacial acetic acid or amalgamated zinc and sodium hydroxide. When $X^1$ is hydroxy, the compound of formula IV is reacted with 1-phenyl-5-chlorotetrazole and the resulting 1-phenyltetrazol-5-yl ether is hydrogenated over palladium on carbon. Alternatively, the compound of formula IV is first reacted with cyanogen bromide in the presence of triethylamine and the reaction product by hydrogenated over palladium on carbon.

Process embodiment (c) provides compounds of formula I wherein n is zero, Z is amino, pyrrolo, pyrrolidino, piperidino, —$NHR^4$, —$N(R^4)_2$, —$NHR^5$, —$NR^4COOR^4$, —$N(R^4)(R^5)$, —$NHCOOR^4$, —$NHCONHR^3$, —$NHCSNHR^3$ or —$NR^3NH_2$ and $R^1$, $R^2$, $R^3$, $R^4$ and $R^5$ are as previously described.

The diazotization of a compound of formula I wherein Z is amino, in accordance with process embodiment (d), can be carried out in a known manner using nitric acid or a nitrite and an acid. Aqueous hydrochloric acid can be used as the solvent for this diazotization. The resulting diazonium salt is then reacted, conveniently without isolation, with sodium azide to give a compound of formula I wherein Z is —$N_3$, or with an amine of the formula $NH(R^4)_2$ to give a compound of formula I wherein Z is —N=N—$N(R^4)_2$, or with an alkali sulfite to give a compound of formula I wherein Z is —NH—$NH_2$.

Process embodiment (e) can be carried out in a manner analogous to that described in the preceding paragraph for the diazotization and yields the compounds of formula I wherein Z is —$N(NO)R^4$.

Examples of groups denoted by $Z^2$ which can be converted by reduction into an amino group, in accordance with process embodiment (f), are nitro, carbobenzoxyamino, —NH—NH—aryl and —N=N—aryl. The reductive conversion of the aforementioned groups into an amino group can be carried out by catalytic hydrogenation; for example, by means of hydrogen and palladium on carbon in an alcohol such as methanol, at a temperature of 10°–50° C., preferably at room temperature.

Groups denoted by $Z^2$ which can be converted by hydrolysis into amino or —$NHR^4$ are, for example, —$NHR^5$, —N=$CHR^7$, —N=$C(R^7)_2$, —N=$CHOR^4$, —$NHCOOR^4$, —$NR^4COOR^4$, —$N(R^4)(R^5)$ and phthalimido ($R^7$ is lower alkyl, lower alkenyl or aryl, and $R^4$ and $R^5$ are as previously described). The hydrolysis of the aforementioned groups is conveniently carried out in an acidic medium, for example, with aqueous or aqueous-alcoholic mineral acids such as hydrochloric acid. Groups denoted by $Z^2$ which can be hydrolyzed under alkaline conditions are —$NR^4COOR^4$, —NH—$COOR^4$ and —NHCHO. The alkaline hydrolysis can be carried out using aqueous or aqueous-alcoholic, for example, methanolic, alkali. The phthalimido group can preferably by converted into an amino group by hydrazinolysis.

The groups denoted by $Z^2$ which are present in the pyrimidine nucleus are preferably hydrolyzable groups, for example, acetylamino, formylamino, phthalimido or carbobenzoxyamino.

Process embodiment (f) provides compounds of formula I wherein n is zero, Z is amino or —$NHR^4$ and $R^1$, $R^2$ and $R^4$ are as previously described.

The alkylation or alkenylation of a compound of formula Ia, in accordance with process embodiment (g), can be carried out using an alkyl halide, such as methyl iodide, or an alkenyl halide, such as allyl bromide, in the presence of a base, for example, sodium methylate or sodium hydride. As the solvent there can be used, for example, dimethylformamide or dimethylsulfoxide.

Process embodiment (g) provides compounds of formula I wherein n is zero, Z is —N($R^4$)($R^5$) or —NR$^4$COOR$^4$ and $R^1$, $R^2$, $R^4$ and $R^5$ are as previously described.

Process embodiment (h) provides compounds of formula I wherein n is zero, Z is —N(alkyl)—NH$_2$ or —N-(alkenyl)—NH$_2$ and $R^1$ and $R^2$ are as previously described.

The N-oxidation, in accordance with process embodiment (i), can be carried out according to known methods using a customary N-oxidizing agent. Preferred N-oxidizing agents are perbenzoic acids, especially m-chloro-perbenzoic acid. The N-oxidation can be carried out, for instance, in an inert solvent, for example, a chlorinated hydrocarbon, such as chloroform or methylene chloride, an alkanol such as methanol or ethanol, dimethylformamide, dimethylsulfoxide, water or dioxane. The oxidation is conveniently carried out at a temperature in the range of from between about room temperature and about the boiling point of the solvent, conveniently, at a temperature in the range of between about 10° C. and about 60° C. A temperature in the range of from about 10° C. to about 20° C. is preferred.

An N-oxide so-obtained can be isolated from the reaction mixture is a known manner. When m-chloroperbenzoic acid or perbenzoic acid is used as the N-oxidizing agent, it has been found convenient to extract the reaction mixture with a weak aqueous-alkaline solution, such as aqueous sodium bicarbonate solution, to acidify the aqueous extract obtained in order to precipitate the excess m-chloroperbenzoic acid or perbenzoic acid and, after removal of the excess acid by filtration, to make the filtrate neutral or slightly basic.

The N-oxidation provides, as a rule, mixtures of $N_1$- and $N_3$-oxides of the formulas

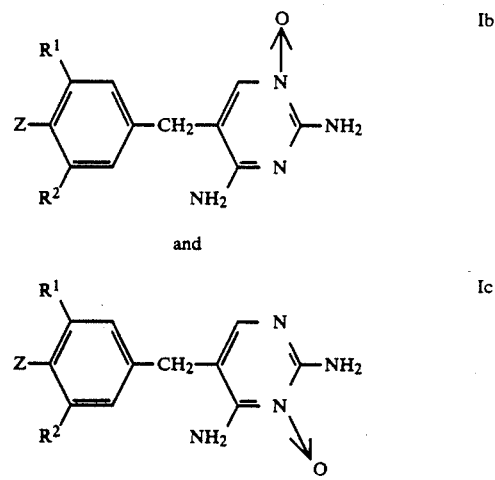

wherein $R^1$, $R^2$ and Z are as previously described.

The separation and purification of the foregoing isomeric products can be carried out by chromatography, for example, column chromatography and/or recrystallization, preferably from polar solvents such as alcohols, water and the like.

The starting materials used in the process embodiments hereinbefore described, insofar as they are not known or insofar as they are not described hereinafter, can be prepared in a manner analogous to that described in the following Examples or according to the methods outlined in the following Table wherein $R^1$, $R^2$, Y and $Z^1$ are as previously described:

TABLE

| Starting Material | Prepared from | Reaction | Literature |
|---|---|---|---|
| IIb IIc | $R^1$—(phenyl with $Z^1$, $R^2$)—CHO + CH$_2$(CN)(CH$_2$Y) | Condensation in strong alkaline medium | Belgian Patent Specifications Nos. 594,131 and 746,846 |
| IIa | IIb | Alkanol addition | |
| III | $R^1$—(phenyl with $Z^1$, $R^2$)—CH$_2$—C(=N–NH$_2$(OH))(C(OH)=N) | Halogenation, if desired, followed by reaction with mercaptans and alkali | Belgian Patent Specification No. 565,002 |
| IV | $R^1$—(phenyl with $Z^1$, $R^2$)—CH$_2$CH(CN)(COOR) | (1) Condensation with guanidine in alkaline medium | DOS 2003578 |
| | | (2) Replacement of the hydroxyl by bromine or chlorine using | |

The compounds of formula I can be converted into acid addition salts, especially those which are customary in pharmaceutical preparations, i.e., pharmaceutically acceptable acid addition salts, by treatment with an inorganic acid, for example, hydrochloric acid, sulfuric acid, phosphoric acid, or the like, or with an organic acid, for example, formic acid, acetic acid, succinic acid, lactic acid, citric acid, maleic acid, fumaric acid, tartaric acid, methanesulfonic acid, p-toluenesulfonic acid or the like.

The benzylpyrimidine derivatives provided by the present invention, that is, the compounds of formula I and their pharmaceutically acceptable acid addition salts, possess antibacterial activity. More particularly, they inhibit bacterial dihydrofolate reductase and potentiate the antibacterial activity of sulfonamides such as sulfisoxazole, sulfadimethoxine, sulfamethoxazole, 4-sulfanilamido-5,6-dimethoxy-pyrimidine, 2-sulfanilamido-4,5-dimethyl-pyrimidine, sulfaquinoxaline, sulfadiazine, sulfamonomethoxine, 2-sulfanilamido-4,5-dimethyl-isoxazole and other inhibitors for enzymes which are involved in the folic acid biosynthesis such as, for example, pteridine derivatives.

For such uses, a combination of one or more of the benzylpyrimidine derivatives of formula I with a sulfonamide can be utilized in a form adapted for oral, rectal or parenteral administration, for example, by incorporating a therapeutic dosage in a conventional dosage form, such as tablets, capsules, elixirs, suspensions, solutions or the like. They can be administered in mixture with conventional pharmaceutical carriers or excipients, such as, for example, corn starch, calcium stearate, magnesium carbonate, calcium silicate, dicalcium phosphate, talc, lactose, and the like. Moreover, they can be administered in the presence of buffers, or agents used to adjust to isotonicity, and the pharmaceutical dosage forms can, if desired, be subjected to conventional pharmaceutical expedients such as, for example, sterilization. The ratio of a compound of formula I to a sulfonamide can vary within a wide range, for example, in the range of from 1:40 (parts by weight) to 5:1 (parts by weight); preferred ratios are between 1:1 and 1:5.

Thus, for example, a tablet can contain 80 mg. of a compound of formula I and 400 mg. of sulfamethoxazole, or it can contain 20 mg. of a compound of formula I and 100 mg. of sulfamethoxazole. A syrup can contain (per 5 ml.) 40 mg. of a compound of formula I and 200 mg. of sulfamethoxazole.

The compounds of formula I possess a high antibacterial activity or a pronounced synergistic effect in combination with sulfonamides. They also have a good compatibility. The compounds of formula I are useful as antibacterial agents alone or in combination with sulfonamides.

The following Examples further illustrate the invention. All temperatures are in degrees Centigrade, unless otherwise described.

EXAMPLE 1

Preparation of α-(2,4p-diamino-5-pyrimidinyl)-2',6'-dimethoxy-p-acetotoluidide

A solution of 1.16 g. of sodium in 300 ml. of absolute ethanol was treated with 9.1 g. of guanidine carbonate and 5.9 g. of 4'-(3-anilino-2-cyano-allyl)-2',6'-dimethoxy-acetanilide and boiled under reflux for 18 hours. Then, the mixture was diluted with 100 ml. of water and the alcohol removed under vacuum. The precipitated α-(2,4-diamino-5-pyrimidinyl)-2',6'-dimethoxy-p-acetotoluidide was removed by filtration under suction, washed with water, recrystallized from methanol/ethyl acetate, and had a melting point of 278°–279° C.

The starting material was prepared as follows:

A solution of 31.5 g. of 4-acetamido-3,5-dimethoxy-toluene in 2 liters of pyridine/water (1:1) was treated portionwise with 142 g. of potassium permanganate over a period of 30 minutes with stirring at 80° C. The mixture was boiled under reflux for 1.5 hours. The manganese dioxide was removed by filtration with suction and washed with 500 ml. of hot water. The filtrate was evaporated to dryness under vacuum at 60° C. and the residue was dissolved in 200 ml. of water. The resulting solution was treated with 2N sodium hydroxide until a strongly alkaline reaction was achieved and then extracted with two 500 ml. portions of ethyl acetate. The ethyl acetate extracts were rejected and the aqueous solution was adjusted to pH 1 with concentrated hydrochloric acid. The precipitated 4-acetamido-3,5-dimethoxy-benzoic acid was removed by filtration with suction, washed with water, recrystallized from methanol-/ethyl acetate and had a melting point of 237°–238° C.

A solution of 20.4 g. of 4-acetamido-3,5-dimethoxy-benzoic acid in 500 ml. of absolute methanol was saturated with dry hydrogen chloride. After standing for 18 hours at room temperature, the solvent was removed under vacuum. The residue was treated with ice-water and with 2N sodium hydroxide until a strongly alkaline reaction was achieved. The resulting emulsion was extracted with two 500 ml. portions of ethyl acetate. The ethyl acetate extracts were washed with two 200 ml. portions of water, combined, dried over magnesium sulfate and evaporated to dryness under vacuum. The residue was dissolved in 400 ml. of absolute tetrahydrofuran. The solution was treated with 40 ml. of absolute pyridine and 40 ml. of acetic anhydride, stirred for 20 hours at room temperature and subsequently evaporated to dryness under vacuum. The residue was treated with 300 ml. of water and extracted with two 600 ml. portions of ethyl acetate. The ethyl acetate extracts were washed with two 200 ml. portions of water, combined, dried over magnesium sulfate and evaporated to dryness in vacuo. The residual 4-acetamido-3,5-dimethoxy-benzoic acid methyl ester was recrystallized from ethyl acetate and had a melting point of 183°–184° C.

A suspension of 30.1 g. of dimethylsulfone and 11.5 g. of sodium hydride (50% dispersion in oil) in 80 ml. of dimethylsulfoxide was stirred at 50° C. for 3 hours with the exclusion of moisture. Then, 20.3 g. of 4-acetamido-3,5-dimethoxybenzoic acid methyl ester were added and the mixture was stirred at room temperature for an additional 20 hours. Thereafter, the solution was diluted with 1 liter of water and extracted with three 1 liter portions of ethyl acetate. The ethyl acetate extracts were washed with two 300 ml. portions of water, combined, dried over magnesium sulfate and evaporated to dryness under vacuum. Recrystallization of the residue from ethyl acetate gave 2',6'-dimethoxy-4'-[(methylsulfonyl-acetyl)]acetanilide having a melting point of 206°–207° C.

A suspension of 10.1 g. of 2',6'-dimethoxy-4'-[(methylsulfonyl-acetyl)]acetanilide and 4.85 g. of sodium borohydride in 400 ml. of ethanol was stirred at room temperature for 18 hours. The solution was treated with 100 ml. of water, and the alciohol was evaporated under vacuum. The precipitated 4'-[(1-hydroxy-2-(methylsulfonyl)-ethyl)]-2',6'-dimethoxy-acetanilide was removed by filtration with suction, recrystallized from methanol/ethyl acetate and had a melting point of 193°–195° C.

A mixture of 3.78 g. of sodium methylate, 5.1 g. of β-anilino-propionitrile and 9.8 g. of 4'-[(1-hydroxy-2-(methylsulfonyl)-ethyl)]-2',6'-dimethoxy-acetanilide in 40 ml. of dimethylsulfoxide was stirred at 50° C. for 4 hours with the exclusion of moisture. The mixture was poured into 400 ml. of water and the resulting emulsion was extracted with three 500 ml. portions of ethyl acetate. The ethyl acetate extracts were washed with two 200 ml. portions of water, combined, dried over magnesium sulfate and evaporated under vacuum. Recrystallization of the residue from ethyl acetate gave 4'-(3-anilino-2-cyano-allyl)-2',6'-dimethoxy-acetanilide having a melting point of 165°–167° C.

EXAMPLE 2

Preparation of 2,4-diamino-5-(4-amino-3,5-dimethoxybenzyl)-pyrimidine dihydrochloride A solution of 10.1 g. of α-(2,4-diamino-5-pyrimidinyl)-2',6'-dimethoxy-p-acetotoluidide in 600 ml. of 1N hydrochloric acid was boiled under reflux for 5 hours and subsequently evaporated to dryness under vacuum. The residue was recrystallized from methanol/ethanol and yielded 2,4-diamino-5-(4-amino-3,5-dimethoxybenzyl)-pyrimidine dihydrochloride, which had a melting point of 286° C. (decomposition).

EXAMPLE 3

Preparation of α-(2,4-diamino-5-pyrimidinyl)-2',6'-dimethoxy-N-methyl-p-acetotoluidide A solution of 1.38 g. of sodium in 300 ml. of absolute ethanol was treated with 10.8 g. of guanidine carbonate and 7.5 g. of 4'-(3-anilino-2-cyano-allyl)-2',6'-dimethoxy-N-methyl-acetanilide and boiled under reflux for 20 hours. The alcohol was removed under vacuum and the residue taken up in a mixture of 100 ml. of water and 20 ml. of ethyl acetate. After stirring at room temperature for 1 hour, the precipitated α-(2,4-diamino-5-pyrimidinyl)-2',6'-dimethoxy-N-methyl-p-acetotoluidide was removed by filtration with suction, washed with water, dried, recrystallized from methanol/ethyl acetate and had a melting point of 262°–264° C.

The starting material was prepared as follows:

A suspension of 12.0 g. of sodium hydride (50% dispersion in oil) in 50 ml. of absolute dimethylformamide was treated with a solution of 46.0 g. of 4-acetamido-3,5-dimethoxy-toluene in 200 ml. of absolute dimethylformamide over a period of 30 minutes with stirring and exclusion of moisture. After stirring at room temperature for 4 hours, 31.2 ml. of methyl iodide were added dropwise over a period of 20 minutes with stirring and ice-cooling. The mixture was stirred at room temperature for 70 hours and subsequently evaporated to dryness under vacuum. The residue was treated with 300 ml. of water and the resulting suspension was extracted with two 500 ml. portions of ethyl acetate. The combined ethyl acetate extracts were washed with 300 ml. of water, dried over magnesium sulfate, filtered and evaporated under vacuum. Recrystallization of the residue from ethyl acetate gave 3,5-dimethoxy-4-(N-methyl-acetamido)-toluene having a melting point of 160°–161° C.

A solution of 42.4 g. of 3,5-dimethoxy-4-(N-methyl-acetamido)-toluene in 2 liters of pyridine/water (1:1) was treated portionwise with 180 g. of potassium permanganate over a period of 1 hour with stirring at 80° C. The mixture was boiled under reflux for an additional hour. Thereafter, the manganese dioxide was removed by filtration with suction and washed with 1 liter of hot water. The filtrate was evaporated to dryness under vacuum. The residue was dissolved in 500 ml. of water and the resulting solution was extracted with 250 ml. of ethyl acetate. The ethyl acetate extract was rejected and the aqueous phase treated with concentrated hydrochloric acid until a strongly acidic reaction was achieved. The precipitated 3,5-dimethoxy-4-(N-methyl-acetamido)-benzoic acid was removed by filtration with suction, washed with water, recrystallized from methanol and had a melting point of 293°–295° C.

A suspension of 35.8 g. of 3,5-dimethoxy-4-(N-methyl-acetamido)-benzoic acid in 500 ml. of absolute methanol was saturated with dry hydrogen chloride, whereby a solution gradually formed. After standing at room temperature for 20 hours, the solution was evaporated to dryness under vacuum. The residue was treated with 200 ml. of ice-water and with a concentrated sodium hydroxide solution until a strongly alkaline reaction was achieved and the resulting emulsion was extracted with two 500 ml. portions of ethyl acetate. The ethyl acetate extracts were washed with two 100 ml. portions of water, combined, dried over magnesium sulfate, filtered and evaporated under vacuum. After recrystallization from ethyl acetate/cyclohexane, the residue yielded 3,5-dimethoxy-4-(N-methylacetamido)- benzoic acid methyl ester having a melting point of 115°–116° C.

A suspension of 35.7 g. of dimethylsulfone and 12.0 g. of sodium hydride (50% dispersion in oil) in 100 ml. of absolute dimethylsulfoxide was stirred at 50° C. for 3 hours with the exclusion of moisture and subsequently treated with 34.0 g. of 3,5-dimethoxy-4-(N-methyl-acetamido)-benzoic acid methyl ester. After stirring at room temperature for 2.25 hours, the mixture was diluted with 1 liter of water. The resulting solution was made acidic with 3N hydrochloric acid and extracted with two 1 liter portions of ethyl acetate. The ethyl acetate extracts were washed with two 200 ml. portions of water, combined, dried over magnesium sulfate and evaporated in vacuo. Recrystallization of the residue from ethyl acetate gave 2',6'-dimethoxy-N-methyl-4'-[(methylsulfonyl)-acetyl]-acetanilide having a melting point of 141°–142° C.

A suspension of 20.9 g. of 2',6'-dimethoxy-N-methyl-4'-[(methylsulfonyl)acetyl]-acetanilide and 9.5 g. of sodium borohydride in 300 ml. of ethanol was stirred at room temperature for 20 hours. The solution was diluted with 300 ml. of water and the alcohol removed under vacuum. The resulting suspension was extracted with two 1 liter portions of ethyl acetate. The ethyl acetate extracts were washed with two 200 ml. portions of water, combined, dried over magnesium sulfate and evaporated under vacuum. Recrystallization of the residue from ethyl acetate gave 4'-[1-hydroxy-2-(methylsulfonyl)-ethyl]-2',6'-dimethoxy-N-methyl-acetanilide having a melting point of 175°–177° C.

A mixture of 3.24 g. of sodium methylate, 8.75 g. of β-anilino-propionitrile and 14.9 g. of 4'-[1-hydroxy-2-(methylsulfonyl)-ethyl]-2',6'-dimethoxy-N-methyl-acetanilide in 60 ml. of absolute dimethylsulfoxide was stirred at 50° C. for 4 hours with the exclusion of moisture. The solution was poured into 600 ml. of water. The resulting emulsion was extracted with two 400 ml. portions of ethyl acetate. Thereafter, the ethyl acetate extracts were washed with two 150 ml. portions of water, combined, dried over magnesium sulfate and evaporated under vacuum. Recrystallization of the residue from ethyl acetate gave 4'-(3-anilino-2-cyano-allyl)-2',6'-dimethoxy-N-methyl-acetanilide having a melting point of 202°–204° C.

EXAMPLE 4

Preparation of 2,4-diamino-5-(4-amino-3,5-dimethoxy-benzyl)-pyrimidine

A solution of 6.9 g. of sodium in 1 liter of absolute ethanol was treated with 54 g. of guanidine carbonate and 31.0 g. of 4-amino-α-(anilino-methylene)-3,5-dimethoxy-hydrocinnamic acid nitrile and boiled under reflux for 20 hours. Then, 500 ml. of water were added and the alcohol was removed under vacuum. After standing at room temperature for 2 hours, the crystallized 2,4-diamino-5-(4-amino-3,5-dimethoxy-benzyl)-pyrimidine was removed by filtration with suction, washed with water, recrystallized from methanol and had a melting point of 215°–216° C.

The starting material was prepared as follows:

13.8 g. of sodium were dissolved in 900 ml. of methanol and to this solution were added 46.8 g. of 3-hydroxy-5-keto-3-cyclohexene-carboxylic acid. The resulting mixture was stirred, maintained between −4° C. and −8° C. by means of a cooling bath and treated over a period of 30 minutes with a phenyl-diazonium chloride solution (prepared from 27.9 g. of aniline, 450 ml. of water, 72 ml. of concentrated hydrochloric acid and 21.0 g. of sodium nitrite in 90 ml. of water). The resulting mixture was stirred for an additional hour at −5° C. to −10° C. The precipitated red reaction product was removed by filtration with suction and washed with about 1000 ml. of water, whereby there was obtained 3-hydroxy-5-keto-4-phenylazo-3-cyclohexene-carboxylic acid having a melting point of 218° C.

60 G. of 3-hydroxy-5-keto-4-phenylazo-3-cyclohexene-carboxylic acid, 200 ml. of methanol, 1200 ml. of benzene and 5 g. of p-toluenesulfonic acid were boiled together under reflux on a water separator for 18 hours. After cooling, the solution was washed with 500 ml. of a 5% sodium bicarbonate solution, then washed with water, dried and evaporated. The residue was dissolved in ethyl acetate and purified on an aluminum oxide column (500 g.; activity stage I). After evaporation of the ethylacetate, there was obtained 3-hydroxy-5-keto-4-phenylazo-3-cyclohexane-carboxylic acid methyl ester as a solid having a melting point of 144° C.

54.8 G. of 3-hydroxy-5-keto-4-phenylazo-3-cyclohexene-carboxylic acid methyl ester, 12.0 g. of acetamide and 2.0 g. of bromosuccinimide were stirred in 600 ml. of chloroform and treated dropwise with 32.0 g. of bromine in 400 ml. of chloroform (the reaction temperature being held below 35° C.). Soon, the separation of acetamide hydrobromide began. The mixture was stirred for an additional 30 minutes at room temperature. Then, the acetamide hydrobromide was removed by filtration and the filtrate evaporated to dryness. The residue was taken up in a small amount of ethanol, filtered under vacuum and washed with ethanol, whereby there was obtained 3,5-dihydroxy-4-phenylazo-benzoic acid methyl ester having a melting point of 216°–218° C.

A mixture of 27.2 g. of 3,5-dihydroxy-4p-phenylazo-benzoic acid methyl ester, 150 ml. of methanol and 64 g. of dimethylsulfate was treated over a period of 45 minutes with a solution of 23 g. of sodium hydroxide in 50 ml. of water with stirring. Care was taken using a cooling bath that the temperature did not exceed 55° C. The mixture was stirred at room temperature for an additional 1 hour, cooled with ice-water, filtered under vacuum and recrystallized from 400 ml. of ethanol, whereby there were obtained red crystals of 3,5-dimethoxy-4-phenylazo-benzoic acid methyl ester having a melting point of 130°–132° C.

12 G. of 3,5-dimethoxy-4-phenylazo-benzoic acid methyl ester were dissolved in 400 ml. of ethanol and, after the addition of 0.80 g. of palladium on carbon, hydrogenated under atmospheric pressure and at room temperature. With slight warming, 2 moles of hydrogen were taken up over a period of 1.5 hours. The catalyst was removed by filtration and the filtrate concentrated under vacuum. The resulting aniline was removed by distillation with steam. After cooling, the 4-amino-3,5-dimethoxy-benzoic acid methyl ester which remained as an aqueous suspension was removed by filtration under vacuum, dried, recrystallized from cyclohexane and had a melting point of 115°–116° C.

A suspension of 214 g. of dimethylsulfone and 78.2 g. of sodium hydride (50% dispersion in oil) in 400 ml. of absolute dimethylsulfoxide was stirred at 50° C. under an atmosphere of nitrogen and exclusion of moisture for 3 hours. The mixture was cooled to 30° C. Thereupon, 137 g. of 4-amino-3,5-dimethoxy-benzoic acid methyl ester were added, and the temperature rose to 50° C. After stirring under an atmosphere of nitrogen and at room temperature for about 1 hour, the resulting mixture was left standing for 3 hours and then dissolved in 2 liters of water with the addition of ice. The solution was adjusted to a pH 6–7 with glacial acetic acid. After stirring under ice-cooling for 1 hour, the crystallized 4'-amino-3',5'-dimethoxy-2-(methylsulfonyl)-acetophenone was removed by filtration with suction, washed with water, dried, recrystallized from ethyl acetate and had a melting point of 166°–167° C.

A suspension of 123 g. of 4'-amino-3',5'-dimethoxy-2-(methylsulfonyl)acetophenone and 68 g. of sodium borohydride in 1.5 liters of alcohol was stirred at room temperature for 20 hours. Thereafter, the suspension was diluted with 1.5 liters of water. The alcohol was evaporated under vacuum and the resulting 4-amino-3,5-dimethoxy-α-[(methylsulfonyl)-methyl]-benzyl alcohol was removed by filtration with suction, washed with water, dried and had a melting point of 178°–179° C.

A mixture of 8.64 g. of sodium methylate, 14.6 g. of β-anilino-propionitrile and 22.0 g. of 4-amino-3,5-dimethoxy-α-[(methylsulfonyl)-methyl]-benzyl alcohol in 50 ml. of absolute dimethylsulfoxide was stirred at 50° C. for 1 hour under an atmosphere of nitrogen and the exclusion of moisture. The solution was poured into 500 ml. of ice-water and the resulting emulsion was extracted with two 500 ml. portions of ethyl acetate. The ethyl acetate extracts were washed with two 250 ml. portions of water, dried over magnesium sulfate and evaporated under vacuum. The residue was dissolved in 60 ml. of ethyl acetate. After standing at room temperature for 20 hours, the crystallized 4-amino-α-(anilino-methylene)-3,5-dimethoxy-hydrocinnamic acid nitrile was removed by filtration with suction, washed with a small amount of ethyl acetate, dried and had a melting point of 150°–151° C.

EXAMPLE 5

Preparation of 4-[(2,4-diamino-5-pyrimidinyl)-methyl]-2,6-dimethoxy-carbanilic acid ethyl ester A solution of 360 mg. of sodium in 100 ml. of absolute ethanol was treated with 2.8 g. of guanidine carbonate and 2.0 g. of 4-(3-anilino-2-cyano-allyl)-2,6-dimethoxy carbanilic acid ethyl ester and boiled under reflux for 20 hours. The solution was diluted with 100 ml. of water and the alcohol removed under vacuum. After standing at room temperature for 1 hour, the precipitate was removed by filtration with suction, washed with water and dissolved in about 200 ml. of boiling ethanol. The solution was chromatographed on 100 g. of silica gel using ethanol/ethyl acetate (1:1) and there was obtained 4-[(2,4-diamino-5-pyrimidinyl)-methyl]-2,6-dimethoxy-carbanilic acid ethyl ester which, after recrystallization from ethanol, had a melting point of 228° C. (decomposition).

The starting material was prepared as follows:

A solution (cooled to 0° C.) of 12.0 g. of 4'-amino-3',5'-dimethoxy-2-(methylsulfonyl)-acetophenone in 100 ml. of absolute pyridine was treated with 5.06 ml. of chloroformic acid ethyl ester with stirring. After stirring at room temperature for 20 hours, the pyridine was removed under vacuum and the residue was taken up in 100 ml. of water. The precipitated 2,6-dimethoxy-4-[(methylsulfonyl)-acetyl]carbanilic acid ethyl ester was removed by filtration with suction, washed with water, recrystallized from ethanol and had a melting point of 192°–193° C.

A suspension of 12.1 g. of 2,6-dimethoxy-4-[(methylsulfonyl)-acetyl]carbanilic acid ethyl ester and 5.3 g. of sodium borohydride in 150 ml. of ethanol was stirred at room temperature for 70 hours. The alcohol was evaporated under vacuum and the residue treated with 150 ml. of water. After standing at room temperature for 1 hour, the crystallized 4-[1-hydroxy-2-(methylsulfonyl)-ethyl]-2,6-dimethoxy-carbanilic acid ethyl ester was removed by filtration with suction, washed with water, recrystallized from ethanol and had a melting point of 168°–170° C.

A mixture of 4.42 g. of sodium ethylate, 5.1 g. of β-anilino-propionitrile and 10.0 g. of 4-[1-hydroxy-2-(methylsulfonyl)-ethyl]-2,6-dimethoxy-carbanilic acid ethyl ester in 150 ml. of dimethylsulfoxide was stirred at 50° C. for 2 hours with the exclusion of moisture. The solution was poured into 1.5 liters of water and the resulting emulsion extracted with two 1 liter portions of ethyl acetate. The ethyl acetate extracts were washed with two 500 ml. portions of water, combined, dried over magnesium sulfate and evaporated under vacuum. The residue was chromatographed on 800 g. of silica gel using methylene chloride/ethyl acetate (3:1) and there was obtained 4-(3-anilino-2-cyano-allyl)-2,6-dimethoxy-carbanilic acid ethyl ester having a melting point of 150°–151° C. (recrystallization from alcohol).

EXAMPLE 6

Preparation of 2,4-diamino-5-(4-amino-3,5-dimethoxy-benzyl)-pyrimidine

A suspension of 1.04 g. of 4-[(2,4-diamino-5-pyrimidinyl)-methyl]-2,6-dimethoxy-carbanilic acid ethyl ester in a mixture of 50 ml. of 4N sodium hydroxide and 50 ml. of ethanol was boiled under reflux for 18 hours, whereby a solution gradually resulted. The alcohol was removed under vacuum. After standing at room temperature for 1 hour, the crystallized 2,4-diamino-5-(4-amino-3,5-dimethoxy-benzyl)-pyrimidine was removed by filtration with suction, washed with water, recrystallized from methanol and had a melting point of 215°–216° C.

EXAMPLE 7

Preparation of 2,4-diamino-5-(4-amino-3,5-dimethoxy-benzyl)-pyrimidine

A solution of 0.1 g. of mercury (II) chloride in 2 ml. of water and 1.5 g. of zinc powder was added to a solution of 1.5 g. of 2,4-diamino-5-(4-amino-3,5-dimethoxy-benzyl)-6-chloropyrimidine in 15.5 ml. of glacial acetic acid and the mixture was boiled under reflux with stirring overnight. Then, the mixture was filtered while hot and the zinc powder washed with 5 ml. of acetic acid. The combined filtrates were added dropwise with stirring at a temperature below 20° C. to 40 ml. of concentrated ammonia. Then, the mixture was stirred at 20° C. for an additional hour and the solid material was removed by filtration under vacuum, washed with water, dried, recrystallized from methanol and there was obtained 2,4-diamino-5-(4-amino-3,5-dimethoxy-benzyl)-pyrimidine having a melting point of 214° C.

The starting material was prepared as follows:

138 G. of 4-amino-3,5-dimethoxy-α-[(methylsulfonyl)-methyl]-benzyl alcohol in 250 ml. of dimethylsulfoxide were treated with 9.75 g. of sodium amide. The mixture was stirred at room temperature for 1.25 hours and then poured into 2 liters of water. The resulting precipitate was extracted with 2 liters of ethyl acetate and the aqueous phase was extracted with 2 liters of ethyl acetate. The combined ethyl acetate phases were washed with two 1 liter portions of deionized water, dried over magnesium sulfate, filtered and evaporated to dryness under vacuum at 40° C. The crystalline residue was dissolved in 250 ml. of hot methanol and the solution treated with 150 ml. of water and left to stand at 4° C. for 18 hours. The crystallized 4-amino-3,5-dimethoxy-benzaldehyde was removed by filtration with suction, washed with a mixture of 40 ml. of methanol and 20 ml. of deionized water and dried under vacuum at 50° C. and had a melting point of 90°-93° C.

A mixture of 18.1 g. of 4-amino-3,5-dimethoxy-benzaldehyde, 11.3 g. of cyanoacetic acid ethyl ester and 3 drops of piperidine was heated at 120° C. for 1 hour in an open vessel, whereby the formed water evaporated. The residue was recrystallized from ethyl acetate/petroleum ether and there was obtained 4-amino-α-cyano-3,5p-dimethoxy-cinnamic acid ethyl ester having a melting point of 134°-136° C.

13.8 G. of 4-amino-α-cyano-3,5-dimethoxy-cinnamic acid ethyl ester were hydrogenated in 500 ml. of ethanol in the presence of 3 g. of palladium on carbon at room temperature and a pressure of 1 atmosphere. After the uptake of the theoretical amount of hydrogen, the reaction was stopped. The catalyst was removed by filtration and the filtrate evaporated under vacuum. The residue was purified by chromatography and there were obtained 10.8 g. of 4-amino-α-cyano-3,5-dimethoxy-hydrocinnamic acid ethyl ester of melting point 77°-78° C. (recrystallization from ethyl acetate/petroleum ether).

13.9 G. of 4-amino-α-cyano-3,5-dimethoxy-hydrocinnamic acid ethyl ester and a guanidine solution (prepared from 1.15 g. of sodium in 50 ml. of ethanol and 5 g. of guanidine hydrochloride) were added to a solution of 1.15 g. of sodium in 50 ml. of ethanol. The mixture was stirred under reflux for 1 hour and evaporated to dryness. The residue was dissolved in a small amount of water and the solution was filtered, made slightly acidic with acetic acid and then made alkaline with sodium bicarbonate. The precipiated 2,6-diamino-5-(4-amino-3,5-dimethoxy-benzyl)-4-pyrimidinol was removed by filtration under vacuum, recrystallized from ethanol/water and had a melting point of 267°-269° C.

2.5 G. of dimethylaniline were added dropwise to a suspension of 2.9 g. of 2,6-diamino-5-(4-amino-3,5-dimethoxy-benzyl)-4-pyrimidinol in 15 ml. of phosphorus oxychloride with stirring. The mixture was brought to boil in 1 hour and then boiled under reflux for 4 hours. Thereafter, 8 to 9 ml. of phosphorus oxychloride were removed by distillation under reduced pressure and the residue was poured on to 80 g. of ice with stirring. The mixture was left to stand at room temperature for 6 days and then 35 ml. of concentrated ammonia were added portionwise. After standing for 2 hours, the solid material was removed by filtration under vacuum, dried, recrystallized from dimethylformamide/ether, whereby there was obtained 2,4-diamino-5-(4-amino-3,5-dimethoxy-benzyl)-6-chloro-pyrimidine having a melting point of 222°-224° C.

EXAMPLE 8

Preparation of 2,4-diamino-5-[3,5-dimethoxy-4-(pyrrol-1-yl)-benzyl]-pyrimidine

A solution of 0.53 g. of sodium in 36 ml. of absolute ethanol was treated with 2.16 g. of guanidine hydrochloride and 3.4 g. of α-(anilino-methylene)-3,5-dimethoxy-4-(pyrrol-1-yl)-hydrocinnamic acid nitrile and boiled for 20 hours under an atmosphere of nitrogen with stirring. The ethanol was removed under reduced pressure and the residue taken up in water, filtered under vacuum, washed with water and recrystallized from ethanol, whereby there was obtained 2,4-diamino-5-[3,5-dimethoxy-4-(pyrrol-1-yl)-benzyl]-pyrimidine having a melting point of 220° C.

The starting material was prepared as follows:

A mixture of 9 g. of diethoxy-tetrahydrofuran and 5 ml. of glacial acetic acid was added dropwise at room temperature to a solution of 10.5 g. of 4-amino-3,5-dimethoxy-benzoic acid methyl ester in 50 ml. of glacial acetic acid with stirring. The mixture was stirred at 100° C. for an additional 30 minutes, cooled with ice, filtered under vacuum, dried and recrystallized from cyclohexane, whereby there was obtained 3,5-dimethoxy-4-(pyrrol-1-yl)-benzoic acid methyl ester having a melting point of 145°-146° C.

A suspension of 2.9 g. of sodium hydride (50% dispersion in oil) and 3.8 g. of dimethylsulfone in 20 ml. of absolute dimethylsulfoxide was stirred at 50° C. for 2 hours under an atmosphere of nitrogen and the exclusion of moisture. Then, heating was stopped and 5.2 g. of 3,5-dimethoxy-4-(pyrrol-1-yl)-benzoic acid methyl ester were added, the temperature rising to 67° C. The mixture was stirred for an additional 2 hours and diluted with 200 ml. of ice-water. The aqueous solution was shaken out with 50 ml. of ethyl acetate, filtered over carbon, made acidic with glacial acetic acid and left to stand overnight in a refrigerator. The precipitated 3',5'-dimethoxy-2-(methylsulfonyl)-4'-(pyrrol-1-yl)-acetophenone was recrystallized from ethyl acetate/petroleum ether and had a melting point of 180° C.

A suspension of 1.54 g. of 3',5'-dimethoxy-2-(methylsulfonyl)-4'-(pyrrol-1-yl)-acetophenone in 20 ml. of ethanol and 20 ml. of water was treated with a solution of 0.4 g. of sodium borohydride in 5 ml. of water with addition of 0.1 g. of sodium hydroxide. The mixture was stirred at room temperature for an additional 3 hours, cooled with ice, diluted with 50 ml. of water and filtered under vacuum. After recrystallization from ethanol, there was obtained 3,5-dimethoxy-α-[(methylsulfonyl)-methyl]-4-(pyrrol-1-yl)-benzyl alcohol having a melting point of 192° C.

A mixture of 2.45 g. of sodium methylate, 9.75 g. of 3,5-dimethoxy-α-[(methylsulfonyl)-methyl]-4-(pyrrol-1-yl)-benzyl alcohol and 6.6 g. of β-anilinopropionitrile in 75 ml. of absolute dimethylsulfoxide was stirred at room temperature for 1 hour under an atmosphere of nitrogen and the exclusion of moisture. Then, the mixture was poured into 250 ml. of ice-cold water and extracted with three 200 ml. portions of ethyl acetate. The ethyl acetate extract was washed with water, dried and evaporated. After chromatography on aluminum oxide and recrystallization from ethanol, there was obtained α-(anilino-methylene)-3,5-dimethoxy-4-(pyrrol-1-yl)-hydrocinnamic acid nitrile having a melting point of 182°-184° C.

EXAMPLE 9

Preparation of 2,4-diamino-5-(4-amino-3,5-diethoxy-benzyl)-pyrimidine

A solution of 0.53 g. of sodium in 36 ml. of ethanol was treated with 2.16 g. of guanidine hydrochloride and 3.2 g. of 4-amino-α-(anilino-methylene)-3,5-diethoxy-hydrocinnamic acid nitrile and the mixture boiled for 20 hours under an atmosphere of nitrogen with stirring. The ethanol was removed under reduced pressure and the residue taken up in water, filtered under vacuum, washed with water, recrystallized from methanol, whereby there was obtained 2,4-diamino-5-(4-amino-3,5-diethoxy-benzyl)-pyrimidine having a melting point of 200°-202° C.

The starting material was prepared as follows:

A solution of 50 g. of sodium hydroxide in 200 ml. of water was added dropwise to a mixture of 54.4 g. of 3,5-dihydroxy-4-phenylazo-benzoic acid methyl ester, 400 ml. of methanol and 86 g. of diethyl sulfate while the temperature was maintained between 40° and 45° C. The mixture was then stirred for 2 hours at room temperature and evaporated to dryness. The residue was shaken with water and ethyl acetate. The organic phase was separated, washed with a sodium carbonate solution and then with water, dried and evaporated. By chromatographic separation and crystallization from methanol, there was obtained 3,5-diethoxy-4-phenylazo-benzoic acid methyl ester having a melting point of 92° C.

6.56 G. of 3,5-diethoxy-4-phenylazo-benzoic acid methyl ester were dissolved in 100 ml. of ethanol and, after the addition of 0.4 g. of palladium on carbon, hydrogenated at atmospheric pressure and at room temperature. With slight warming, 2 moles of hydrogen were taken up. The catalyst was removed by filtration and the filtrate concentrated under vacuum. The aniline formed was distilled with steam. After cooling, the 4-amino-3,5-diethoxy-benzoic acid methyl ester which remained as an aqueous suspension was removed by filtration under vacuum, dried, recrystallized from cyclohexane and had a melting point of 90°-92° C.

A suspension of 3.76 g. of dimethylsulfone and 2.88 g. of sodium hydride (50% dispersion in oil) in 20 ml. of absolute dimethylsulfoxide was stirred at 50° C. for 2 hours under an atmosphere of nitrogen and the exclusion of moisture. The heating was stopped and 4.78 g. of 4-amino-3,5-diethoxy-benzoic acid methyl ester were added. The mixture was heated to 90° C. for 1 minute. Then, it was stirred at room temperature for 1.5 hours and diluted with 100 ml. of ice-water. The aqueous solution was shaken with 50 ml. of ethyl acetate, filtered over carbon, made acidic with glacial acetic acid, filtered under vacuum and the resulting 4'-amino-3',5'-diethoxy-2-(methylsulfonyl)-acetophenone was recrystallized from ethyl acetate and had a melting point of 161°-163° C.

A suspension of 26 g. of 4'-amino-3',5'-diethoxy-2-(methylsulfonyl)-acetophenone in 350 ml. of ethanol and 350 ml. of water was treated with a solution of 7.0 g. of sodium borohydride in 90 ml. of water. There was also added 0.5 g. of sodium hydroxide. The mixture was stirred for 17 hours at room temperature, cooled with ice, diluted with 500 ml. of water and filtered under vacuum. After recrystallization from methanol, there was obtained 4-amino-3,5-diethoxy-α-[(methylsulfonyl)-methyl]-benzyl alcohol having a melting point of 166°-168° C.

A mixture of 0.82 g. of sodium methylate, 3.0 g. of 4-amino-3,5-diethoxy-α-[(methylsulfonyl)methyl]-benzyl alcohol and 2.2 g. of β-anilino-propionitrile in 12.5 ml. of absolute dimethylsulfoxide was stirred at 55° C. under an atmosphere of nitrogen and the exclusion of moisture for 5 hours, poured into 100 ml. of water and extracted with three 100 ml. portions of ethyl acetate. The ethyl acetate extract was washed with water, dried and evaporated. After chromatography on aluminum oxide and recrystallization from ethyl acetate/petroleum ether, there was obtained 4-amino-α-(anilino-methylene)-3,5-diethoxy-hydrocinnamic acid nitrile having a melting point of 179°-181° C.

EXAMPLE 10

Preparation of 2,6-diallyloxy-α-(2,4-diamino-5-pyrimidinyl)-p-acetotoluidide

A solution of 0.26 g. of sodium in 20 ml. of ethanol was treated with 1.08 g. of guanidine hydrochloride and 1.9 g. of 2',6'-bis(allyloxy)-4'-(3-anilino-2-cyanoallyl)-acetanilide and boiled under nitrogn with stirring for 20 hours. The ethanol was removed under reduced pressure. The residue was taken up in water, removed by filtration under vacuum, washed with water, and recrystallized from methanol/water, whereby there was obtained 2,6-diallyloxy-α-(2,4-diamino-5-pyrimidinyl)-p-acetotoluidide having a melting point of 176°-177° C.

The starting material was prepared as follows:

A mixture of 27 g. of 3,5-dihydroxy-4-phenylazo-benzoic acid methyl ester, 250 ml. of glacial acetic acid and 21 g. of acetic anhydride was stirred at 100° C. for 3 hours, complete solution occurring. The resulting solution was evaporated to dryness under reduced pressure. The residue was taken up in methanol and again evaporated to dryness. The residue was recrystallized from dimethylformamide/methanol and there was obtained 3-acetoxy-5-hydroxy-4-phenylazo-benzoic acid methyl ester having a melting point of 162° C.

30 G. of 3-acetoxy-5-hydroxy-4-phenylazo-benzoic acid methyl ester were dissolved in 500 ml. of methanol and, after the addition of 3 g. of palladium on carbon, hydrogenated at atmospheric pressure and room temperature. With slight warming, 2 moles of hydrogen were taken up. The catalyst was removed by filtration and the filtrate concentrated under vacuum. The aniline formed was distilled with steam. After cooling, the 4-acetamido-3,5-dihydroxy-benzoic acid methyl ester which remained as an aqueous suspension was filtered under vacuum, dried, recrystallized from ethyl acetate/petroleum ether and had a melting point of 202°-203° C.

A mixture of 11.25 g. of 4-acetamido-3,5-dihydroxy-benzoic acid methyl ester, 12.1 g. of allyl bromide, 15 g. of dry potassium carbonate and 100 ml. of acetone was boiled and stirred on a reflux condenser for 17 hours. The acetone was removed by distillation. The residue was taken up in water/ethyl acetate. Thereafter, the organic phase separated, washed with water, dried and evaporated. After recrystallization from ethyl acetate/petroleum ether, there was obtained 4-acetamido-3,5-diallyloxy-benzoic acid methyl ester having a melting point of 135°-137° C.

A suspension of 3.76 g. of dimethylsulfone and 2.9 g. of sodium hydride (50% dispersion in oil) in 20 ml. of absolute dimethylsulfoxide was stirred at 50° C. under an atmosphere of nitrogen and the exclusion of moisture for 2 hours. The heating was stopped and 3.0 g. of 4-acetamido-3,5-diallyloxy-benzoic acid methyl ester were added while the temperature rose to 58° C. The mixture was then stirred at room temperature for 2 hours and diluted with 200 ml. of ice-water. The aqueous solution was extracted with 50 ml. of ethyl acetate, filtered over carbon, made acidic with glacial acetic acid and left in a refrigerator for 2 hours. The precipitated 2',6'-bis(allyloxy)-4'-[(methylsulfonyl-acetyl]-acetanilide was recrystallized from methanol and had a melting point of 196°-197° C.

A suspension of 1.7 g. of 2',6'-bis(allyloxy)-4'-[(methylsulfonyl)-acetyl]-acetanilide in 20 ml. of ethanol and 20 ml. of water was treated with a solution of 0.40 g. of sodium borohydride in 5 ml. of water. There was also added 0.1 g. of sodium hydroxide. The mixture was stirred for 3 hours at room temperature and evaporated to dryness. The residue was taken up in water, removed by filtration under vacuum, dried and recrystallized from ethyl acetate/petroleum ether, whereby there was obtained 2',6'-bis(allyloxy)-4'-[1-hydroxy-2-(methylsulfonyl)ethyl]-acetanilide having a melting point of 162° C.

A mixture of 1.4 g. of sodium methylate, 3.75 g. of β-anilino-propionitrile and 6.3 g. of 2',6'-bis(allyloxy)-4'-[1-hydroxy-2-(methylsulfonyl)-ethyl]-acetanilide in 43 ml. of absolute dimethylsulfoxide was stirred at room temperature under an atmosphere of nitrogen and the exclusion of moisture for 3 hours, poured into 200 ml. of water and extracted with ethyl acetate. The ethyl acetate extract was washed with water, dried and evaporated. After chromatography on aluminum oxide and recrystallization from ethanol, there was obtained 2',6'-bis-(allyloxy)-4'-(3-anilino-2-cyano-allyl)-acetanilide having a melting point of 176°-178° C.

EXAMPLE 11

Preparation of 2,4-diamino-5-(4-amino-3,5-dimethoxy-benzyl)-pyrimidine

A mixture of 6.5 g. of sodium methylate, 21.6 g. of guanidine carbonate and 12.8 g. of α-(4-amino-3,5-dimethoxy-benzyl)-4-morpholino-acrylonitrile in 120 ml. of absolute dimethylsulfoxide was stirred at 120° C. for 60 hours. Subsequently, the mixture was diluted with 1.2 liters of water and extracted with two 2 liter portions of ethyl acetate. The ethyl acetate extract was washed with two 1 liter portions of water, dried over magnesium sulfate and evaporated under vacuum. After recrystallization of the residue from methanol, there was obtained 2,4-diamino-5-(4-amino-3,5-dimethoxy-benzyl)-pyrimidine having a melting point of 215°-216° C.

The starting material was prepared as follows:

A mixture of 8.1 g. of sodium methylate and 21.0 g. of β-morpholinopropionitrile in 100 ml. of absolute dimethylsulfoxide was treated during 10 minutes with a solution of 18.1 g. of 4-amino-3,5-dimethoxy-benzaldehyde in 50 ml. of absolute dimethylsulfoxide with stirring at 60° C. After stirring at 60° C. for 30 minutes, the mixture was poured into 1.5 liters of water and the precipiate was extracted with two 1 liter portions of ethyl acetate. The ethyl acetate extract was washed with two 500 ml. portions of water, dried over magnesium sulfate and evaporated under vacuum. 35 G. of crystalline residue was obtained which was triturated with 40 ml. of alcohol. After standing for 2 hours at 4° C., the residue was removed by filtration under suction, washed with a small amount of ice-cold alcohol and dried, whereby there was obtained α-(4-amino-3,5-dimethoxy-benzyl)-4-morpholino-acrylonitrile having a melting point of 128°-129° C.

EXAMPLE 12

Preparation of 2,4-diamino-5-(4-amino-3,5-dimethoxy-benzyl)-pyrimidine

A solution of 1.3 g. of sodium in 200 ml. of absolute alcohol was treated with 10.3 g. of guanidine carbonate and 5 g. of 4-amino-3,5-dimethoxy-α-(ethoxymethyl)-cinnamic acid nitrile and boiled under reflux for 48 hours. After the addition of 200 ml. of water, the alcohol was removed under vacuum and the mixture was then extracted with two 500 ml. portions of ethyl acetate. The insoluble material was separated and rejected. The ethyl acetate extract was washed with 200 ml. of water, dried over magnesium sulfate and evaporated under vacuum. The residue was chromatographed on 90 g. of silica gel using ethyl acetate/methanol (3:1), whereby there was obtained 2,4-diamino-5-(4-amino-3,5-dimethoxy-benzyl)-pyrimidine, having a melting point of 215°–216° C. (recrystallization from methanol).

The starting material was prepared as follows:

A solution of 4.6 g. of sodium in 400 ml. of absolute alcohol was treated with 18.1 g. of 4-amino-3,5-dimethoxy-benzaldehyde and 19.8 g. of β-ethoxy-propionitrile and refluxed for 20 hours. Then, the mixture was evaporated to dryness under vacuum. The resulting residue was dissolved in a mixture of 1.2 liters of ethyl acetate and 300 ml. of water with stirring. After separation of the phases, the ethyl acetate extract was washed with 300 ml. of water, dried over magnesium sulfate and evaporated to dryness under vacuum. The residue was chromatographed on 1 kg. of silica gel using ethyl acetate/methylene chloride (1:9), and there was obtained 4-amino-3,5-dimethoxy-α-(ethoxy-methyl)-cinnamic acid nitrile having a melting point of 54°–55° C. (recrystallization from alcohol/water).

EXAMPLE 13

Preparation of 2,4-diamino-5-(4-amino-3,5-dimethoxy-benzyl)-pyrimidine

A solution of 1.84 g. of sodium in 200 ml. of absolute alcohol was treated with 14.4 g. of guanidine carbonate and 8.9 g. of 4'-(3-anilino-2-cyano-allyl)-2',6'-dimethoxy-formanilide and refluxed for 20 hours. Then, 200 ml. of water were added and the alcohol was removed under vacuum. After standing at room temperature for 2 hours, the crystals formed were removed by filtration with suction, washed with water and recrystallized from methanol, whereby there was obtained 2,4-diamino-5-(4-amino-3,5-dimethoxy-benzyl)-pyrimidine having a melting point of 215°–216° C.

The starting material was prepared as follows:

A solution (cooled to 10° C.) of 18.1 g. of 4-amino-3,5-dimethoxy-benzaldehyde in 210 ml. of 98% formic acid was treated dropwise with 70 ml. of acetic anhydride with stirring and the temperature was maintained below 15° C. The solution was then stirred for 2 hours at room temperature, treated with 80 ml. of water and evaporated to dryness under vacuum. The residue was washed with water, recrystallized from alcohol and there was obtained 2',6'-dimethoxy-4'-formyl-formanilide having a melting point of 159°–160° C.

A mixture of 2.7 g. of sodium methylate, 3.65 g. of β-anilino-propionitrile and 4.2 g. of 2',6'-dimethoxy-4'-formyl-formanilide in 30 ml. of absolute dimethylsulfoxide was stirred at 50° C. for 30 minutes. The solution was poured into 500 ml. of water and the resulting emulsion extracted with two 500 ml. portions of ethyl acetate. The ethyl acetate extract was washed with two 300 ml. portions of water, dried over magnesium sulfate and evaporated under vacuum. The residue was recrystallized from ethyl acetate and there was obtained 4'-(3-anilino-2-cyano-allyl)-2',6'-dimethoxy-formanilide having a melting point of 186°–187° C.

EXAMPLE 14

Preparation of 2,4-diamino-5-(4-amino-3,5-dimethoxy-benzyl)-pyrimidine hydrochloride A solution of 2.75 g. of 2,4-diamino-5-(4-amino-3,5-dimethoxy-benzyl)-pyrimidine in 50 ml. of methanol was treated with 10 ml. of 1N hydrochloric acid. The resulting precipitate was dissolved by warming and the solution evaporated at 60° C. under vacuum to about 20 ml. After standing at room temperature for 2 hours, the precipitate was removed by filtration with suction, washed with methanol and dried, whereby there was obtained 2,4-diamino-5-(4-amino-3,5-dimethoxybenzyl)-pyrimidine hydrochloride having a melting point of 296° C. (decomposition).

EXAMPLE 15

Preparation of 2,4-diamino-5-(4-azido-3,5-dimethoxy-benzyl)-pyrimidine

A solution of 7 g. of 2,4-diamino-5-(4-amino-3,5-dimethoxy-benzyl)-pyrimidine dihydrochloride in 60 ml. of 1N hydrochloric acid and 40 ml. of water was treated over a period of 5 minutes with stirring and ice-cooling with a solution of 1.52 g. of sodium nitrite in 10 ml. of water. After stirring at 0° C. for 30 minutes, a solution of 1.43 g. of sodium azide in 20 ml. of water was added. The solution was stirred at 0° C. for 2 hours and then treated with sodium bicarbonate to obtain an alkaline reaction. After stirring at 0° C. for 1 hour, the precipitate was removed by filtration with suction, washed with water and recrystallized from methanol, whereby there was obtained 2,4-diamino-5-(4-azido-3,5-dimethoxy-benzyl)-pyrimidine having a melting point of 152° C. (decomposition).

EXAMPLE 16

Preparation of 2,4-diamino-5-[4-(3,3-diethyl-1-triazeno)-3,5-dimethoxybenzyl]pyrmidine A solution of 7 g. of 2,4-diamino-5-(4-amino-3,5-dimethoxy-benzyl)-pyrimidine dihydrochloride in 60 ml. of 1N hydrochloric acid and 40 ml. of water was treated during 5 minutes with stirring and ice-cooling with a solution of 1.52 g. of sodium nitrite in 10 ml. of water. The solution was stirred at 0° C. for 30 minutes and 14.6 g. of diethylamine were then added. After stirring with ice-cooling for 2 hours, the precipitate was removed by filtration with suction, washed with water and recrystallized from methanol, whereby there was obtained 2,4-diamino-5-[4-(3,3-diethyl-1-triazeno)-3,5-dimethoxy-benzyl]-pyrimidine having a melting point of 196°–197° C. (decomposition).

EXAMPLE 17

Preparation of
4-[(2,4-diamino-5-pyrimidinyl)-methyl]-2,6-dimethoxy-N-methyl-carbanilic acid ethyl ester A mixture of 8.7 g. of 4-[(2,4-diamino-5-pyrimidinyl)-methyl]-2,6-dimethoxy-carbanilic acid ethyl ester and 1.44 g. of sodium hydride (50% dispersion in oil) in 75 ml. of absolute dimethylformamide was stirred at room temperature for 1 hour and then treated with 4.26 g. of methyl iodide. After stirring at room temperature for 3 hours, the dimethylformamide was removed at 60° C. under vacuum. The residue was dissolved in a mixture of 500 ml. of ethyl acetate and 150 ml. of water. After separation of the phases, the aqueous phase was extracted with 500 ml. of ethyl acetate. The combined ethyl acetate extracts were washed with 300 ml. of water, dried over magnesium sulfate and evaporated under vacuum. After recrystallization of the residue from alcohol, there was obtained 4-[(2,4-diamino-5-pyrimidinyl)-methyl]-2,6-dimethoxy-N-methyl-carbanilic acid ethyl ester having a melting point of 187°-188° C.

EXAMPLE 18

Preparation of
N-ethyl-4-[(2,4-diamino-5-pyrimidinyl)-methyl]-2,6-dimethoxycarbanilic acid ethyl ester A mixture of 12 g. of 4-[(2,4-diamino-5-pyrimidinyl)-methyl]-2,6-dimethoxycarbanilic acid ethyl ester and 2 g. of sodium hydride (50% dispersion in oil) in 100 ml. of absolute dimethylformamide was stirred at room temperature for 4 hours and then treated with 6.5 g. of ethyl iodide. After stirring at room temperature for 30 minutes, the dimethylformamide was removed at 60° C. under vacuum. The residue was taken up in 250 ml. of water and the precipitated product extracted with two 600 ml. portions of ethyl acetate. The ethyl acetate extract was washed with two 300 ml. portions of water, dried over magnesium sulfate and evaporated under vacuum. The residue was chromatographed on 350 g. of silica gel using ethyl acetate/alcohol (3:1) and there was obtained N-ethyl-4-[(2,4-diamino-5-pyrimidinyl)-methyl]-2,6-dimethoxy-carbanilic acid ethyl ester having a melting point of 165°-167° C. (recrystallization from ethyl acetate).

EXAMPLE 19

Preparation of
2,4-diamino-5-[4-(dimethylamino)-3,5-dimethoxy-benzyl]-pyrimidine A solution of 414 mg. of sodium in 100 ml. of absolute alcohol was treated with 3.24 g. of guanidine carbonate and 2 g. of α-(anilino-methylene)-4-(dimethylamino)-3,5-dimethoxy-hydrocinnamic acid nitrile and refluxed for 20 hours. After the addition of 50 ml. of water, the alcohol was removed under vacuum. The precipiate was removed by filtration with suction, washed with water and recrystallized from methanol, whereby there was obtained 2,4-diamino-5-[4-(dimethylamino)-3,5-dimethoxy-benzyl]-pyrimidine having a melting point of 218°-219° C.

The starting material was prepared as follows:

48 G. of dimethylsulfate were added dropwise over a period of 30 minutes with stirring at room temperature to a suspension of 40 g. of 4-amino-3,5-dimethoxybenzoic acid methyl ester and 130 g. of anhydrous potassium carbonate in 1.7 liters of anhydrous tetrahydrofuran. Then, the mixture was refluxed for 18 hours with stirring. The tetrahydrofuran was evaporated under vacuum and the residue treated with 600 ml. of water. The precipitated product was extracted with two 600 ml. portions of ethyl acetate and the extract was washed with two 300 ml. portions of water, dried over magnesium sulfate and evaporated under vacuum. The residue was chromatographed on 1.5 kg. of silica gel using methylene chloride/ethyl acetate (9:1) and there was obtained 4-(dimethylamino)-3,5-dimethoxybenzoic acid methyl ester having a melting point of 71°-72° C. (recrystallization from cyclohexane).

A suspension of 21.6 g. of dimethylsulfone and 7.7 g. of sodium hydride (50% dispersion in oil) in 80 ml. of absolute dimethylsulfoxide was stirred at 50° C. for 3 hours under an atmosphere of nitrogen and the exclusion of moisture. The mixture was cooled to 30° C. and 15.6 g. of 4-(dimethylamino)-3,5-dimethoxybenzoic acid methyl ester were added. After stirring at room temperature for 4 hours, 500 ml. of water were added and the solution was made neutral with glacial acetic acid. The precipitate was removed by filtration with suction, washed with water, dried, recrystallized from ethyl acetate/cyclohexane, whereby there was obtained 4'-(dimethylamino)-3',5'-dimethoxy-2-(methylsulfonyl)-acetophenone having a melting point of 111°-112° C.

A suspension of 24 g. of 4'-(dimethylamino)-3',5'-dimethoxy-2-(methylsulfonyl)-acetophenone and 12.1 g. of sodium borohydride in 260 ml. of alcohol was stirred at room temperature for 16 hours, whereby a solution was obtained. After the addition of 260 ml. of water, the alcohol was evaporated under vacuum. The precipitate was removed by filtration with suction, washed with water and recrystallized from ethyl acetate, whereby there was obtained 4-(dimethylamino)-3,5-dimethoxy-α-[(methylsulfonyl)-methyl]-benzyl alcohol having a melting point of 147°-148° C.

A mixture of 3.3 g. of sodium methylate, 8.9 g. of β-anilino-propionitrile and 15.7 g. of 4-(dimethylamino)-3,5-dimethoxy-α[(methylsulfonyl)-methyl]-benzyl alcohol in 40 ml. of absolute dimethylsulfoxide was stirred at 50° C. under an atmosphere of nitrogen for 2 hours. The mixture was poured into 400 ml. of water and the resulting emulsion was extracted with two 400 ml. portions of ethyl acetate. The ethyl acetate extract was washed with two 200 ml. portions of water, dried over magnesium sulfate and evaporated under vacuum. After recrystallization of the residue from ethyl acetate, there was obtained α-(anilino-methylene)-4-(dimethylamino)-3,5-dimethoxy-hydrocinnamic acid nitrile having a melting point of 130°-132° C.

EXAMPLE 20

Preparation of 2,4-diamino-5-[3,5-dimethoxy-4(methylamino)-benzyl]-pyrimidine

A solution of 1.29 g. of sodium in 200 ml. of absolute alcohol was treated with 10 g. of guanidine carbonate and 6 g. of α-(anilino-methylene)-3,5-dimethoxy-4-(methylamino)-hydrocinnamic acid nitrile and refluxed for 20 hours. Subsequently, 200 ml. of water were added and the alcohol was evaporated under vacuum. After standing at room temperature for 2 hours, the precipitate was removed by filtration with suction, washed with water and recrystallized from alcohol, whereby there was obtained 2,4-diamino-5-[3,5-dimethoxy-4-(methylamino)-benzyl]-pyrimidine having a melting point of 204° C.

The starting material was prepared as follows:

A solution of 50.6 g. of 4-amino-3,5-dimethoxy-benzoic acid methyl ester in 1 liter of absolute pyridine was treated during 30 minutes with 82 g. of carbobenzoxy chloride with stirring and ice-cooling. Thereafter, the mixture was stirred at room temperature for 20 hours. The pyridine was evaporated under vacuum and the residue treated with 1 liter of water and 3N hydrochloric acid to obtain a strongly acidic reaction. The resulting emulsion was extracted with two 1.5 liter portions of ethyl acetate. The ethyl acetate extract was washed with two 800 ml. portions of water, dried over magnesium sulfate and evaporated under vacuum. After recrystallization of the residue from ethyl acetate, there was obtained 2,6-dimethoxy-4-(methoxy-carbonyl)-carbanilic acid benzyl ester having a melting point of 132°-133° C.

A suspension of 34.2 g. of 2,6-dimethoxy-4-(methoxy-carbonyl)-carbanilic acid benzyl ester and 5.8 g. of sodium hydride (50% dispersion in oil) in 300 ml. of absolute dimethylformamide was stirred at room temperature for 4 hours. The resulting solution was treated with 17 g. of methyl iodide with stirring and ice-cooling. After stirring at room temperature for 1 hour, the dimethylformamide was removed under vacuum at 60° C. Then, 1 liter of water was added to the residue and the emulsion was extracted with two 2 liter portions of ethyl acetate. The organic phases were washed with two 1 liter portions of water, dried over magnesium sulfate and evaporated under vacuum. After recrystallization of the residue from alcohol, there was obtained 2,6-dimethoxy-4-(methoxy-carbonyl)-N-methyl-carbanilic acid benzyl ester having a melting point of 130°-131° C.

A suspension of 33.5 g. of 2,6-dimethoxy-4-(methoxy-carbonyl)-N-methylcarbanilic acid benzyl ester in 1 liter of methanol was hydrogenated in the presence of 1.5 g. of palladium on carbon (5%) until the hydrogen uptake stopped. The suspension was heated to boiling and filtered. The filtrate was evaporated under vacuum and the residue recrystallized from cyclohexane, whereby there was obtained 3,5-dimethoxy-4-(methylamino)-benzoic acid methyl ester having a melting point of 49°-51° C.

A suspension of 44.2 g. of dimethylsulfone and 16 g. of sodium hydride (50% dispersion in oil) in 150 ml. of absolute dimethylsulfoxide was stirred at 50° C. for 4 hours under an atmosphere of nitrogen and the exclusion of moisture. 30.4 g. of 3,5-dimethoxy-4-(methylamino)-benzoic acid methyl ester were added and the mixture was stirred at 80° C. for 10 minutes and at 25° C. for 30 minutes. The mixture was then dissolved in 600 ml. of water and the solution was made neutral by the addition of glacial acetic acid. The precipitate was removed by filtration with suction, washed with water, dried and recrystallized from ethyl acetate, whereby there was obtained 3',5'-dimethoxy-4'-(methylamino)-2-(methylsulfonyl)-acetophenone having a melting point of 98°-99° C.

A suspension of 31 g. of 3',5'-dimethoxy-4'-(methylamino)-2-(methylsulfonyl)-acetophenone and 16.3 g. of sodium borohydride in 600 ml. of ethanol was stirred at room temperature for 16 hours. The solution was diluted with 600 ml. of water and the alcohol was removed by distillation under vacuum. The crystals formed were filtered with suction, washed with water and dried, whereby there was obtained 3,5-dimethoxy-4-(methylamino)-α-[(methylsulfonyl)-methyl]-benzyl alcohol having a melting point of 141°-142° C.

A mixture of 2.7 g. of sodium methylate, 7.3 g. of β-anilino-propionitrile and 12 g. of 3,5-dimethoxy-4-(methylamino)-α-[(methylsulfonyl)-methyl]-benzyl alcohol in 100 ml. of absolute dimethylsulfoxide was stirred at 50° C. under an atmosphere of nitrogen for 30 minutes and then poured into 1 liter of water. The resulting emulsion was extracted with two 1 liter portions of ethyl acetate. The ethyl acetate extract was washed with two 5000 ml. portions of water, dried over magnesium sulfate and evaporated under vacuum. After recrystallization of the residue from ethyl acetate, there was obtained α-(anilino-methylene)-3,5-dimethoxy-4-(methylamino)-hydrocinnamic acid nitrile having a melting point of 150°-152° C.

EXAMPLE 21

Preparation of 2,4-diamino-5-[3,5-dimethoxy-4-(methyl-nitrosoamino)-benzyl]-pyrimidine A solution of 2.9 g. of 2,4-diamino-5-[3,5-dimethoxy-4-(methylamino)-benzyl]-pyrimidine in 40 ml. of 1N hydrochloric acid was treated dropwise with a solution of 830 mg. of sodium nitrite in 10 ml. of water with stirring and ice-cooling. The mixture was stirred for 3 hours at room temperature and then sodium carbonate was added to obtain an alkaline reaction. The precipitate was removed by filtration with suction, washed with water and recrystallized from methanol, whereby there was obtained 2,4-diamino-5-[3,5-dimethoxy-4-(methyl-nitrosoamino)-benzyl]-pyrimidine having a melting point of 249°-250° C. (decomposition).

EXAMPLE 22

Preparation of 2,4-diamino-5-[4-ethylamino)-3,5-dimethoxy-benzyl]-pyrimidine

A solution of 4.3 g. of sodium in 1 liter of absolute alcohol was treated with 33.6 g. of guanidine carbonate and 21 g. of α-(anilino-methylene)-4-(ethylamino)-3,5-dimethoxy-hydrocinnamic acid nitrile and refluxed for 20 hours. After cooling, 1 liter of water was added and the alcohol was removed under vacuum. The precipitate was removed by filtration with suction, washed with water and recrystallized from alcohol, whereby there was obtained 2,4-diamino-5-[4-(ethylamino)-3,5-dimethoxy-benzyl]-pyrimidine having a melting point of 186°-188° C.

The starting material was prepared as follows:

A suspension of 103 g. of 2,6-dimethoxy-4-(methoxy-carbonyl)-carbanilic acid benzyl ester and 17.3 g. of sodium hydride (50% dispersion in oil) in 1 liter of absolute dimethylformamide was stirred at room temperature for 4 hours and subsequently treated with 56.2 g. of ethyl iodide with stirring and ice-cooling. After stirring at room temperature for 30 minutes, the dimethylformamide was removed at 60° C. under vacuum. Then, 1 liter of water was added to the residue and the mixture was extracted with two 1.5 liter portions of ethyl acetate. The ethyl acetate extract was washed with two 700 ml. portions of water, dried over magnesium sulfate and evaporated under vacuum. After recrystallization of the residue from alcohol, there was obtained N-ethyl-2,6-dimethoxy-4-(methoxy-carbonyl)-carbanilic acid benzyl ester having a melting point of 85°-86° C.

A suspension of 77.5 g. of N-ethyl-2,6-dimethoxy-4-(methoxy-carbonyl)-carbanilic acid benzyl ester in 1 liter of methanol was hydrogenated in the presence of 2 g. of palladium on carbon (5%) until hydrogen uptake ceased. The suspension was heated to boiling and filtered. The filtrate was evaporated under vacuum. After recrystallization of the residue from cyclohexane, there was obtained 4-(ethylamino)-3,5-dimethoxy-benzoic acid methyl ester having a melting point of 50°-51° C.

A suspension of 58.4 g. of dimethylsulfone and 21.1 g. of sodium hydride (50% dispersion in oil) in 200 ml. of absolute dimethylsulfoxide was stirred at 50° C. under an atmosphere of nitrogen and the exclusion of moisture for a period of 4 hours. Then, 42.6 g. of 4-(ethylamino)-3,5-dimethoxy-benzoic acid methyl ester were added. The resulting mixture was stirred at 80° C. for 10 minutes and subsequently dissolved in 1 liter of water. The solution was neutralized with glacial acetic acid. The precipitate was removed by filtration with suction, washed with water, dried and recrystallized from ethyl acetate, whereby there was obtained 4'-(ethylamino)-3',5'-dimethoxy-2-(methylsulfonyl)-acetophenone having a melting point of 129°-130° C.

A suspension of 48 g. of 4'-(ethylamino)-3',5'-dimethoxy-2-(methylsulfonyl)-acetophenone and 23.8 g. of sodium borohydride in 1 liter of alcohol was stirred at room temperature for 20 hours, resulting in a solution. After the addition of 1 liter of water, the alcohol was evaporated under vacuum. The crystals formed were removed by filtration with suction, washed with water and dried, whereby there was obtained 4-(ethylamino)-3,5-dimethoxy-α-[(methylsulfonyl)-methyl]-benzyl alcohol having a melting point of 121°-122° C.

A mixture of 8.9 g. of sodium methylate, 24.1 g. of β-anilino-propionitrile and 41.5 g. of 4-(ethylamino)-3,5-dimethoxy-α-[(methylsulfonyl)-methyl]-benzyl alcohol in 200 ml. of absolute dimethylsulfoxide was stirred under an atmosphere of nitrogen at 50° C. for 20 minutes. The mixture was poured into 2 liters of water and the resulting emulsion was washed with two 1 liter portions of water, dried over magnesium sulfate and evaporated under vacuum. After recrystallization of the residue from ethyl acetate, there was obtained α-(anilino-methylene)-4-(ethylamino)-3,5-dimethoxy-hydrocinnamic acid nitrile having a melting point of 128°-130° C.

EXAMPLE 23

Preparation of 2,4-diamino-5-(4-amino-3,5-dimethyl-benzl)-pyrimidine

A solution of 1.95 g. of sodium in 500 ml. of absolute alcohol was treated with 15.3 g. of guanidine carbonate and 9.3 g. of 4-amino-α-(anilino-methylene)-3,5-dimethyl-hydrocinnamic acid nitrile and refluxed for 40 hours. 500 Ml. of water were added and the alcohol was removed under vacuum. The precipitate was removed by filtration with suction, washed with water and recrystallized from methanol, whereby there was obtained 2,4-diamino-5-(4-amino-3,5-dimethyl-benzyl)-pyrimidine having a melting point of 258°-260° C.

The starting material was prepared as follows:

A suspension of 33 g. of dimethylsulfone and 11 g. of sodium hydride (50% dispersion in oil) in 160 ml. of absolute dimethylsulfoxide was stirred at 50° C. under an atmosphere of nitrogen and the exclusion of moisture for 3 hours. Then, 18 g. of 4-amino-3,5-dimethyl-benzoic acid methyl ester were added. The mixture was stirred at 80° C. for 30 minutes and at room temperature for 1 hour and then dissolved in 400 ml. of water. The solution was neutralized with glacial acetic acid. The precipitate which formed was removed by filtration with suction, washed with water, dried and recrystallized from ethyl acetate, whereby there was obtained 4'-amino-3',5'-dimethyl-2-(methylsulfonyl)-acetophenone having a melting point of 179°-180° C.

A suspension of 16.5 g. of 4'-amino-3',5'-dimethyl-2-(methylsulfonyl)-acetophenone and 10.6 g. of sodium borohydride in 500 ml. of alcohol was stirred at room temperature for 20 hours, resulting in a solution. After the addition of 500 ml. of water, the alcohol was evaporated under vacuum and the mixture was extracted with two 1 liter portions of ethyl acetate. The ethyl acetate extract was washed with two 500 ml. portions of water, dried over magnesium sulfate and evaporated under vacuum. After crystallization of the residue from ether, there was obtained 4-amino-3,5-dimethyl-α-[(methylsulfonyl)-methyl]-benzyl alcohol having a melting point of 146°-148° C.

| -continued | |
|---|---|
| Capsule formulation: | Per Capsule |
| Total Weight | 270 mg |

Procedure

The ingredients are mixed with an aqueous pharmacoat 603 solution in a suitable mixer. The moist mass is granulated, dried and sieved. The mixture is then filled into hard shell gelatine capsules on a capsulating machine.

We claim:

1. A compound, 2,4-diamino-5-(4-amino-3,5-dimethoxybenzyl)-pyrimidine or a pharmaceutically acceptable acid addition salt thereof.

2. A compound in accordance with claim 1, 2,4-diamino-5-(4-amino-3,5-dimethoxybenzyl)-pyrimidine monohydrochloride.

3. A compound in accordance with claim 1, 2,4-diamino-5-(4-amino-3,5-dimethoxybenzyl)-pyrimidine dihydrochloride.

4. A compound, 2,4-diamino-5-[4-(dimethylamino)-3,5-dimethoxy-benzyl]-pyrimidine, or a pharmaceutically acceptable acid addition salt thereof.

* * * * *